(12) United States Patent
Amis et al.

(10) Patent No.: US 10,624,755 B2
(45) Date of Patent: Apr. 21, 2020

(54) PROSTHETIC GLENOID COMPONENT

(71) Applicant: Imperial Innovations Limited, London (GB)

(72) Inventors: Andrew Amis, London (GB); Diogo Geraldes, London (GB); Roger John Hart Emery, London (GB); Ulrich N. Hansen, London (GB)

(73) Assignee: Imperial Innovations Limited, London (GB)

( * ) Notice: Subject to any disclaimer, the term of this patent is extended or adjusted under 35 U.S.C. 154(b) by 0 days.

(21) Appl. No.: 15/561,389

(22) PCT Filed: Mar. 23, 2016

(86) PCT No.: PCT/GB2016/050807
§ 371 (c)(1),
(2) Date: Sep. 25, 2017

(87) PCT Pub. No.: WO2016/151320
PCT Pub. Date: Sep. 29, 2016

(65) Prior Publication Data
US 2018/0104065 A1    Apr. 19, 2018

(30) Foreign Application Priority Data
Mar. 26, 2015  (GB) .................................. 1505212.9

(51) Int. Cl.
*A61F 2/40*      (2006.01)
*A61B 17/17*    (2006.01)
*A61F 2/30*      (2006.01)

(52) U.S. Cl.
CPC ........ *A61F 2/4081* (2013.01); *A61B 17/1778* (2016.11); *A61F 2002/3069* (2013.01);
(Continued)

(58) Field of Classification Search
CPC ............ A61F 2/4081; A61F 2002/3069; A61F 2002/3085; A61F 2002/30878; A61F 2002/30889
See application file for complete search history.

(56) References Cited

U.S. PATENT DOCUMENTS 5,800,551 A    9/1998  Williamson et al.
6,364,910 B1   4/2002  Shultz et al.
(Continued)

OTHER PUBLICATIONS

International Search Report and Written Opinion, PCT International Application No. PCT/GB2016/050807, PCT/ISA/210, PCT/ISA/220, PCT/ISA/237, dated Jul. 25, 2016.
(Continued)

*Primary Examiner* — Brian A Dukert
(74) *Attorney, Agent, or Firm* — Saliwanchik, Lloyd & Eisenschenk (57) ABSTRACT

A prosthetic glenoid component (10) comprising a concave external bearing surface (12), a glenoid-contacting surface (14) opposite to the bearing surface, and a plurality of fixation elements (16) protruding from said glenoid-contacting surface (14) oppositely to said bearing surface (12) for location into a peripheral portion (104b) of a glenoid cavity (104) to secure the component to the scapula (102), wherein a central portion (15) of the glenoid-contacting surface (14) is free of fixation elements so as to preserve the integrity of the glenoid vault.

19 Claims, 7 Drawing Sheets

(52) U.S. Cl.
    CPC ............... *A61F 2002/30604* (2013.01); *A61F 2002/30878* (2013.01); *A61F 2002/30881* (2013.01)

(56) References Cited

U.S. PATENT DOCUMENTS

| | | | |
|---|---|---|---|
| 2007/0055380 A1* | 3/2007 | Berelsman | A61F 2/4081 623/19.11 |
| 2010/0249938 A1 | 9/2010 | Gunther et al. | |
| 2012/0130499 A1* | 5/2012 | Long | A61F 2/30734 623/19.11 |
| 2012/0239051 A1 | 9/2012 | De Wilde et al. | |
| 2014/0005789 A1* | 1/2014 | Chavarria | A61F 2/4081 623/19.11 |
| 2014/0257495 A1 | 9/2014 | Goldberg | |
| 2016/0045323 A1* | 2/2016 | Kovacs | A61F 2/4081 623/19.11 |

OTHER PUBLICATIONS

Combined Search and Examination Report under Sections 17 and 18(3), UK Intellectual Property Office, Application No. GB1505212.9, dated Aug. 25, 2015.

\* cited by examiner

PROSTHETIC GLENOID COMPONENT

CROSS-REFERENCE TO RELATED APPLICATIONS

This application is a national stage application of International Application No. PCT/GB2016/050807, filed Mar. 23, 2016, which claims priority to Great Britain Application No. 1505212.9, filed Mar. 26, 2015, the disclosures of both of which are incorporated herein by reference in their entirety, including any figures, tables, and drawings.

FIELD OF THE INVENTION

The present invention relates generally to prosthetic glenoid components. In particular, but not exclusively, the invention relates to ways in which to fit such components securely in position on a patient's scapula.

BACKGROUND TO THE INVENTION

Patient-specific prostheses having one or more contoured surfaces to match with one or more of: a bone surface surrounding the area in which the prosthesis will be secured; a corresponding articular bone surface; and a surface that has been resected to receive the prosthesis, are known. The contoured surface(s) may be determined pre-operatively, through techniques including the use of computer-assisted image methods based on three-dimensional images of the patient's anatomy reconstructed from MRI, CT, ultrasound, X-ray, or other three- or two-dimensional medical scans of the patient's anatomy, to ensure that the prosthesis fits closely to the existing bone surface once located in position during a surgical procedure.

In particular, prosthetic glenoid components having a generally concave external bearing surface, to match the articular surface of a patient's associated humeral head, are known. On the opposite side to the bearing surface, a glenoid-contacting surface has one or more fixation elements protruding from it for location into the glenoid cavity in order to secure the component to the scapula. To date, at least one relatively large fixation element has been provided approximately centrally, for location in a corresponding central region of the glenoid cavity and penetrating deep into the glenoid vault.

These are typically secured in position according to the following standard operating procedure:

1. A deltopectoral incision is made along the anterior edge of the deltoid muscle (although other approaches also possible: posterior, superior, minimally invasive, etc.);
2. A resulting lateral skin flap is mobilised;
3. The fascia is incised, and exposed veins, nerves and deltoid muscle are retracted;
4. The rotator cuff is split;
5. Good exposure of the humeral head is achieved through antero-superior dislocation of the joint. Sometimes, tenotomy is required when dislocation is difficult to achieve;
6. The humeral head is resected of to increase space for glenoid preparation;
7. A k-wire is inserted centrally as a guide for a reamer and a drill guide;
8. A size-dependent reamer is then used to prepare a bone tunnel to receive the central fixation element;
9. A drill guide is positioned over the k-wire and manually aligned;
10. A drill sleeve is inserted and a first anchoring hole is drilled;
11. A fixation peg is used to prevent guide rotation;
12. At least a second anchoring hole is secured;
13. The instruments are removed;
14. An appropriate trial glenoid component is selected and the correct sized glenoid is determined;
15. If it is a cemented procedure, the holes are filled with bone cement;
16. The glenoid is pushed/impacted into the prepared bone;
17. Wait for cement to settle.

Figure 1:
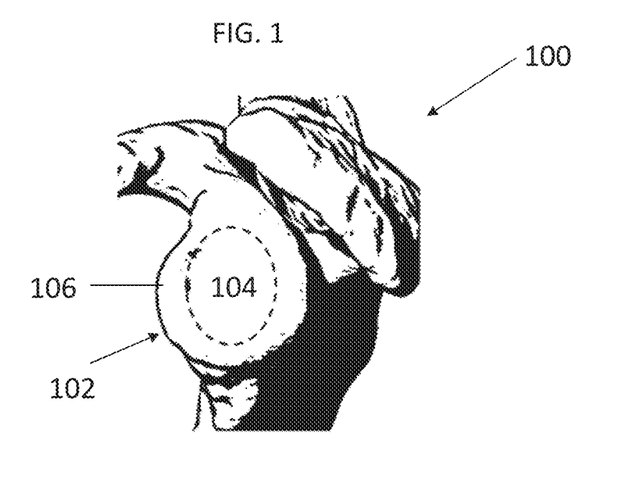
FIG. 1 shows a close-up end-on view of a glenoid.

An exemplary scapula 100 is shown in FIG. 1, zoomed in on the glenoid 102. As is well known, the glenoid 102 comprises a generally concave glenoid cavity 104 surrounded by a glenoid rim 106. Glenoids 102 come in a variety of different sizes and shapes, but are typically tear-drop shaped, as seen in FIG. 1.

Figure 5:
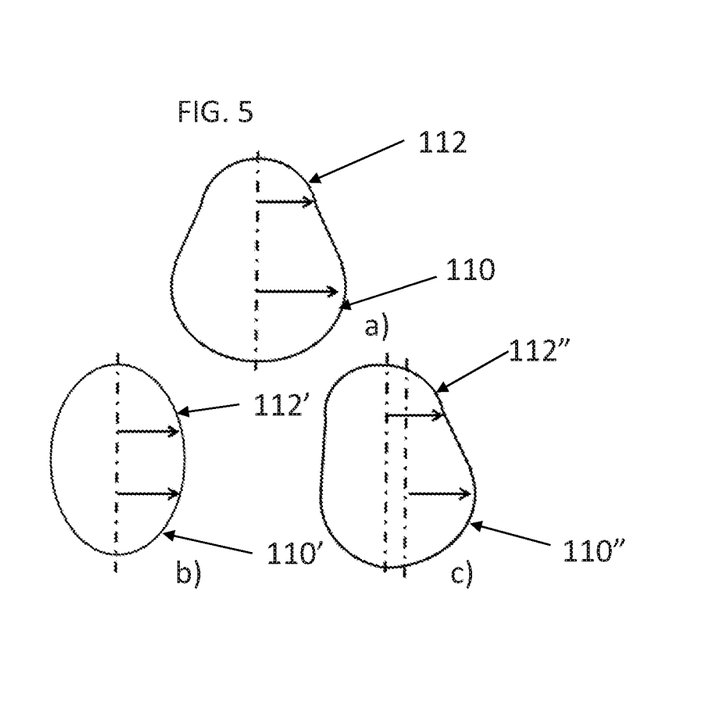
FIG. 5 shows, schematically, some different profiles that the prosthetic glenoid component can have.

Prosthetic glenoid components therefore likewise come in a variety of different sizes and with differing shapes to best suit a patient's needs. Anatomically-shaped components can be provided, to accurately match a particular patient's glenoid shape. Alternatively, components having an optimal shape to suit a wide range of different glenoid shapes can be provided. Suitable generic shapes include: pear-shaped, in which a lower portion 110 has a larger radius than an upper portion 112, along a common vertical axis, as seen in FIG. 5a for example; oval, with upper and lower portions 110'; 112' sharing a common radius size, as seen in FIG. 5b for example; and tear-drop shaped, in which a lower portion 110" has a larger radius than an upper portion 112", but horizontally offset from it, forming an asymmetric shape as seen in FIG. 5c.

Due to the relatively small size of prosthetic glenoid components (for example in comparison to larger prosthetic components as used to replace other articular surfaces, such as the humeral head, or articular surfaces in the knee or hip, for example) and lack of bone support due to the topography of the scapula and especially the glenoid region thereof, it has proven difficult to provide reliable, strong, long-term fixation of such prosthetic glenoid components to the underlying glenoid cavity. Moreover, these difficulties are exacerbated by the fact that the central fixation element acts as a pivot for non-central forces acting on the component, thereby inducing rocking forces that function as a loosening mechanism, weakening the fixation of the component to the underlying bone. Also, the central fixation element projects into a hollow portion of the bone, so typically requires reinforcement through a cemented fixation. Where there is a cemented fixation, the repeated rocking motions serve to fracture the cement and therefore loosen the attachment of the component to the bone. Also, in cementless applications, the relatively large micromotion induced between the implant and the bone results in a lack of osseointegration.

Figure 2:
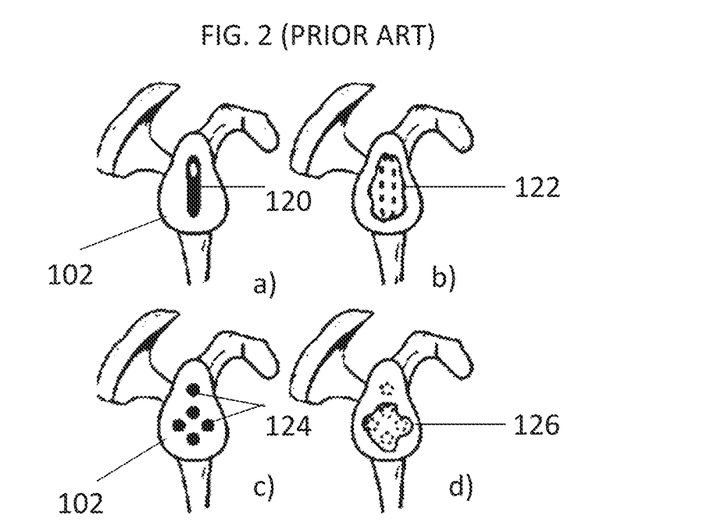

An object of the invention is therefore to provide a more secure attachment of a prosthetic glenoid component to the underlying glenoid bone surface.

Where a prosthetic glenoid component becomes loose, as described above, it needs to be replaced through revision surgery. Such revision surgery is difficult because of the damage caused to the glenoid cavity 104 by the loosening glenoid component and the fact that a larger fixation element is needed to make a secure connection. This can lead to a sink-hole effect during revision surgery, whereby the weak central portion of the glenoid cavity 104 is destroyed as the primary component is removed (bone attached to the primary component's central fixation element either by cement or by bone in-growth comes out together with the component) and thus loses structural viability for reliably securing the revision component. This is shown in FIG. 2, in which FIG. 2a shows a glenoid 102 to which has been secured a primary prosthetic glenoid component having a central keel 120, and FIG. 2b shows a resulting sink-hole 122; FIG. 2c shows an alternative form of known primary fixation, using a plurality of pegs 124, with a resulting sink-hole 126 being shown in FIG. 2d.

Another object of the invention is therefore to provide a prosthetic glenoid component that allows for better revision procedures.

A further object of the invention is to provide a prosthetic glenoid component that is sufficiently small as to be implanted through minimally invasive procedures.

SUMMARY OF THE INVENTION

According to a first aspect of the invention, defined by the accompanying claim 1, there is provided a prosthetic glenoid component comprising:
- a concave external bearing surface;
- a glenoid-contacting surface opposite to the bearing surface; and
- a plurality of fixation elements protruding from said glenoid-contacting surface oppositely to said bearing surface for location into a peripheral portion of a glenoid cavity to secure the component to the scapula, wherein a central portion of the glenoid-contacting surface is free of fixation elements.

According to a second aspect of the invention, there is provided a prosthetic glenoid component comprising:
- a concave external bearing surface;
- a glenoid-contacting surface opposite to the bearing surface; and
- a plurality of fixation elements protruding from said glenoid-contacting surface oppositely to said bearing surface for location into a peripheral portion of a glenoid cavity to secure the component to the scapula, wherein all fixation elements protruding from said glenoid-contacting surface are of a common size.

The component may have a superior end with a first radius of curvature and an inferior end with a second radius of curvature, larger than the first radius of curvature. The respective centres of the first and second radii of curvature may be co-linear along a superior-inferior axis of the component.

The component may be symmetrical about a superior-inferior axis. Alternatively, one of the respective centres of the first and second radii of curvature may be off-set from a superior-inferior axis of the component.

At least the glenoid-contacting surface may be sized and shaped to substantially match the geometry of a patient's resected glenoid cavity.

The fixation elements preferably comprise pegs. The pegs each typically comprise a root portion adjacent to said glenoid-contacting surface and a stem portion. The root portion may be wider than the stem portion. An interface between the root portion and the glenoid-contacting surface may be fileted.

The pegs may each further comprise a head portion at a free end thereof. The root, stem and head portions may be contiguous with one another. The head portion may be chamfered. The head portion may be wider than the stem portion. Alternatively, the head portion may be narrower than the root portion.

At least the stem portion may be tapered, narrowing away from the root portion.

The pegs may each comprise a central axial core and a plurality of circumferential ribs disposed along the length of the core. The ribs are typically disposed over at least the stem portion. The diameter of at least one of the ribs on the stem portion may be greater than the diameter of the root portion.

At least one of the ribs may be disposed on the head portion.

The ribs may all have the same diameter.

At least one of the ribs may be barbed.

The ribs have a width to length ratio in the range of less than 1:1.

The pegs preferably have a diameter to length ratio in the range of 2:1 to 1:2, more preferably close to 1:1.

The pegs may extend parallel to one another. Alternatively, in certain embodiments the pegs may diverge from one another.

In some embodiments, there are six pegs.

The pegs may be arranged substantially equidistantly from an outer edge of the component. In certain embodiments, though, and in particular for larger-sized components, the pegs may not all be at the same distance from the outer edge.

The objective is for the pegs to be anchored around the periphery of the glenoid and strongly into the shallow subchondral bone layer to a depth of less than 10 mm, preferably approximately 5 to 6 mm.

The fixation elements may be arranged dependent on patient-specific metrics.

The component may be wedge shaped, having a thicker depth at one side relative to an opposite side.

The component may be manufactured from one or more materials selected from: stainless steel, cobalt chromium, titanium, and suitable alloys thereof; ceramic; Silicon nitride; pyrocarbon; carbon-reinforced PEEK; PEEK, PE (VitaE PE, Xlink PE, Normal PE), and PCU. It is known for glenoid prostheses to have two layers; typically a metal backing and a polymeric bearing surface. Components according to certain embodiments may take such a multi-layered form.

The component may further comprise an osseo-conductive coating on at least one of the glenoid-contacting surface and the plurality of fixation elements.

According to a third aspect of the invention, there is provided an inventory of prosthetic glenoid components for attachment to differently shaped resected glenoid cavities, each component as defined in the first or second aspects of the invention, wherein at least one of the fixation elements in each component across the inventory is positioned in a common reference location. Preferably, at least two of the fixation elements in each component across the inventory are positioned in common reference locations a specific fixed distance apart.

According to a fourth aspect of the invention, there is provided a guide for preparing a patient's glenoid cavity to receive a prosthetic glenoid component according to the first or second aspects of the invention, the guide comprising:
- a body with a glenoid-contacting surface matching that of the prosthetic glenoid component; and
- a plurality of guide apertures extending through the body and positioned in registration with the respective locations of the plurality of fixation elements on the prosthetic glenoid component, for guiding a drill bit, in use, to drill fixation holes in the patient's glenoid cavity to accommodate said plurality of fixation elements.

The guide apertures typically have a depth in the range of 5 mm to 20 mm.

According to a fifth aspect of the invention, there is provided a kit comprising:
- a prosthetic glenoid component according to any of the first or second aspects of the invention; and
- an associated guide according to the fourth aspect of the invention.

The kit may further comprise an associated drill bit sized for receipt through the guide apertures for drilling said fixation holes.

BRIEF DESCRIPTION OF DRAWINGS

Embodiments of the present invention will now be described, by way of example only, with reference to the accompanying drawings, in which:

FIG. 2 illustrates problems associated with known central fixation systems, in which FIGS. 2a and 2b illustrate a fin-type fixation element and a resulting sink-hole in a central portion of the glenoid cavity, whereas FIGS. 2c and 2d illustrate peg-type fixation elements and a resulting sink-hole in a central portion of the glenoid cavity;

FIG. 5a representing a pear shape; FIG. 5b an oval; and FIG. 5c a 'teardrop' shape;

FIGS. 11a-c depict a guide according to another aspect of the invention, for use in drilling holes to receive the fixation pegs of a prosthetic glenoid component: FIG. 11a being a perspective view; FIG. 11b being a side view; and FIG. 11c being a plan view.

DETAILED DESCRIPTION

Figure 3:
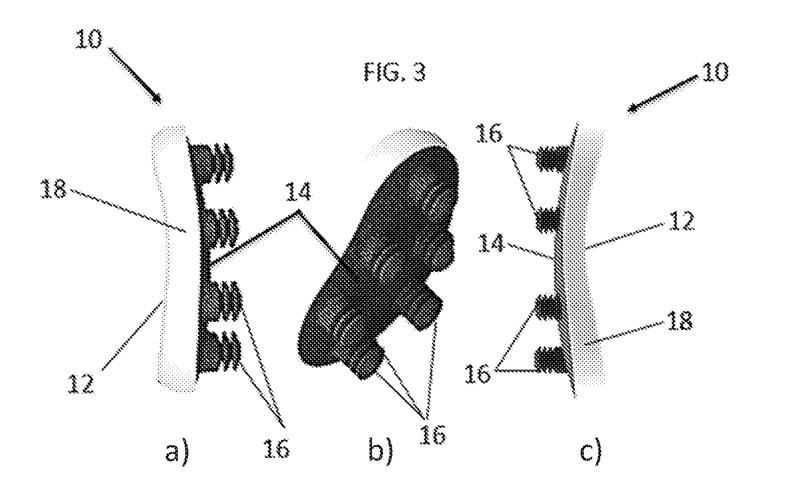
FIG. 3 shows a prosthetic glenoid component according to one aspect of the invention, in various orientations to illustrate the location of the fixation pegs.
Figure 4:
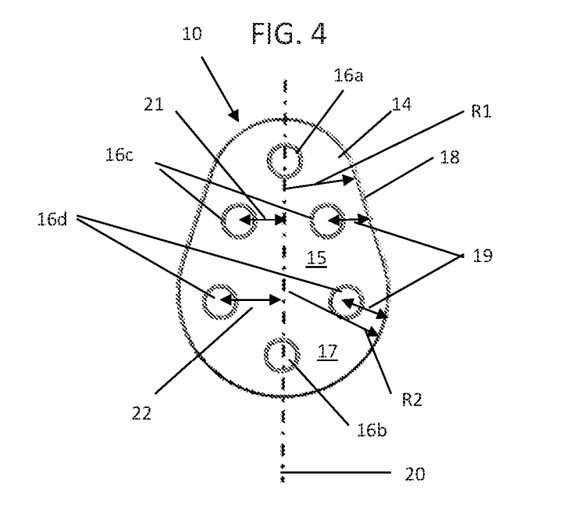
FIG. 4 is a schematic underside view of a prosthetic glenoid component according to one embodiment of the invention, having a 'pear-shaped' profile and with a particular fixation peg arrangement.

A prosthetic glenoid component 10 according to an embodiment is shown in FIGS. 3 and 4. The component 10 as illustrated is of the pear-shaped type described above in respect of the prior art and the invention will be described in this context. It will be appreciated that the invention may equally be applied to components of other general shapes, such as oval or tear-drop.

The component 10 comprises a generally concave external bearing surface 12, contoured to substantially match the articular surface of a patient's associated humeral head (as is known in the art, there is usually a mismatch between the curvature of the humeral head and the glenoid in order to allow for translations to take place). A glenoid-contacting surface 14 is on the opposite side to the bearing surface 12, and has a plurality of pegs 16 protruding from it for location into corresponding holes in the glenoid cavity 104 in order to secure the component to the scapula. The component 10 has a depth defined by a side wall 18 extending between the bearing surface 12 and the glenoid-contacting surface 14.

The side wall 18 defines an outline profile for the component 10 and this will usually be selected to match the shape of the patient's glenoid 102 as closely as possible, as explained in greater detail below. The illustrated component 10 has a superior-inferior axis 20 and has a superior end with a first radius of curvature R1 and an inferior end with a second radius of curvature R2, larger than the first radius of curvature. The respective centres of the first and second radii of curvature R1, R2 may be co-linear along the superior-inferior axis 20, such that the outline profile of the component is symmetrical about that axis. Alternatively, one of the respective centres of the first and second radii of curvature R1, R2 may be off-set from the superior-inferior axis 20.

To date, at least one peg, stem or other fixation element has been provided in a central portion 15 of the glenoid-contacting surface 14, for location in a corresponding central region 104a of the glenoid cavity 104. However, the component 10 has no such fixation elements 16 within the central portion 15 of the glenoid contacting-surface 14; rather, each of the pegs 16 is located in a peripheral portion 17 of the glenoid contacting-surface. Accordingly, each peg 16 is positioned for location in a peripheral portion 104b of the glenoid cavity 104.

The subchondral glenoid bone is stronger at the periphery than centrally and accordingly by providing pegs 16 only within the peripheral portion 104b and using fixation elements that penetrate to a lesser depth a stronger, more reliable attachment between the glenoid component 10 and the subchondral bone can be made, sparing the underlying glenoid vault and thus reducing the possibility of the above-described sink-hole effects. Moreover, by moving the fixation points towards the periphery, the above-described problems associated with induced rocking motions due to central fixation can be avoided.

In the illustrated exemplary component 10, there are six pegs 16 located with approximately even spacings therebetween about the peripheral portion 17 of the glenoid-contacting surface 14. The pegs are positioned between 1 and 5 mm from the edge of the component, in particular 2 to 4 mm, and more specifically 3 mm. As perhaps best seen in FIG. 4, the pegs 16 are each located at an approximately equal distance 19 in from the side wall 18. The pegs 16 are arranged symmetrically, with superior and inferior pegs 16a, 16b positioned on the superior-inferior axis 20, a superior middle pair of pegs 16c spaced a first distance 21 from the axis, and an inferior middle pair of pegs 16d spaced a second distance 22 from the axis. The second distance 22 is marginally greater than the first distance 21, to account for the pear-shaped outline of the component 10 and to keep the distances 19 approximately equal.

Figure 9:
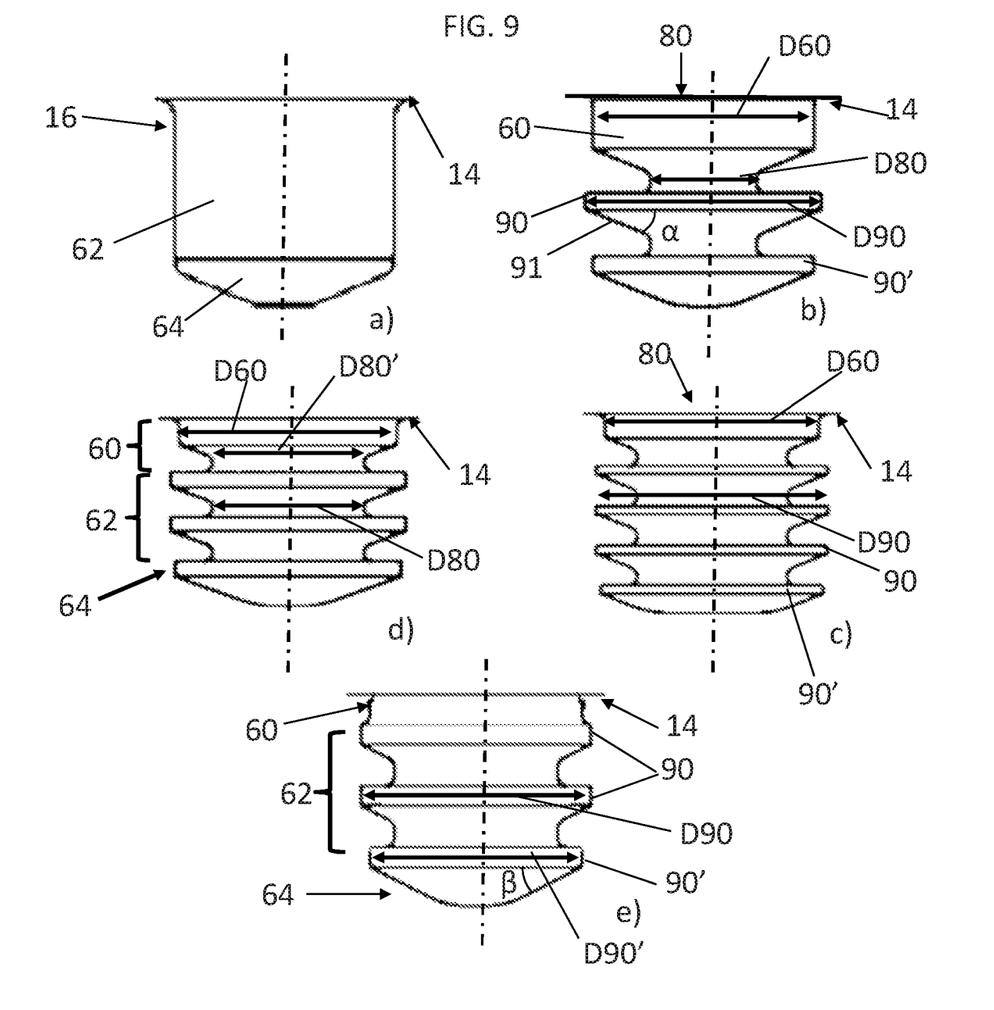
FIGS. 9a-9e depict different peg designs according to embodiments of the invention.

In comparison to fixation pegs known from the prior art, the pegs 16 are short, having a preferred diameter to length ratio of approximately 1:1. In some embodiments, the ratio may be in the range of 2:1 to 1:2. Various different exemplary peg configurations are shown in FIGS. 9 and 10.

The following table sets out exemplary approximate sizes for the component, where the width is defined as the maximum dimension transverse to the axis 20—e.g. R2, and where the length is defined as the maximum dimension parallel to the axis 20:

| Size | Width (mm) | Length (mm) |
| --- | --- | --- |
| 1 | 23 | 30 |
| 2 | 26 | 34 |
| 3 | 29 | 38 |
| 4 | 32 | 42 |

Figure 10:
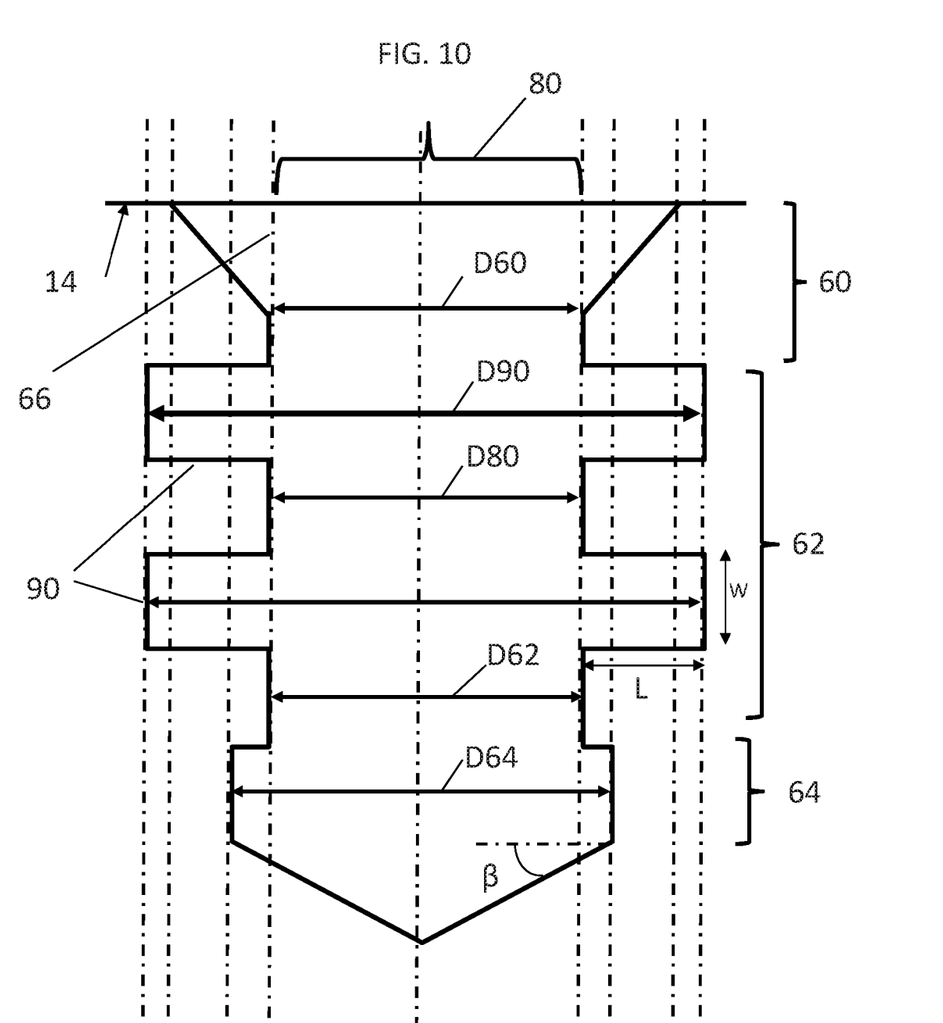
FIG. 10 is a further, schematic, view of a peg.

FIG. 10 shows a peg comprising: a root portion 60 adjacent to the glenoid-contacting surface 14; a stem portion 62; and a head portion 64 at a free end of the peg, remote from the glenoid-contacting surface 14. The root 60, stem 62 and head 64 portions are contiguous with one another. The root portion 60 has a diameter $D_{60}$, the stem portion 62 has a diameter $D_{62}$ and the head portion 64 has a diameter $D_{64}$. The head portion 64 is chamfered, with an angle β. In some embodiments, there is no chamfer; the angle β would be zero. The interface between the root portion 60 and the glenoid-contacting surface 14 is fileted 66 so as to minimise stress-raisers in that area and has been optimised to reduce spring-back of the implant (i.e. the implant coming out of the bone surface due to elastic reaction from the peg threads) to <2 mm, ideally <1 mm, more specifically <=0.5 mm. Spring back should be minimised in order to reduce the implant-bone gap and improve chances of bone growth.

The peg comprises a central axial core 80 and a plurality of circumferential ribs 90 disposed along the length of the core 80, in particular the stem portion 62 thereof. The central axial core 80 has a diameter $D_{80}$ and the ribs 90 on the stem portion have a diameter $D_{90}$. The ribs 90 have a thickness, or axial width, W, and a length L—defined as the distance from the core 80 to the free end of the rib. The ribs typically have a width to length ratio of <1:1 to achieve better fixation through elastic deformation of the ribs.

The pegs 16 can range in length (i.e. distance from the glenoid-contacting surface 14 to the tip at the head 64) between 1 and 10 mm, more specifically 3 to 8 mm, ideally 4 to 6 mm, and most preferably 5 mm.

FIG. 9a shows a plain peg 16 without ribs. It has a straight-sided stem 62 and a chamfered head 64. The part of the stem closest to the glenoid-contacting surface 14 can be considered as a root portion 60, contiguous with the stem. The root, stem and head portions are all of a common diameter; albeit that the head 64 is chamfered.

FIG. 9b shows an alternative design in which the root portion 60 has a diameter $D_{60}$ equal to the diameter $D_{90}$ of the circumferential rib 90 on the stem portion 62 and of the rib 90' on the head portion 64. The core 80 has a smaller diameter $D_{80}$. This embodiment provides improved push-in/pull-out ratios; it has a good rib length to width ratio whilst allowing for enough space between the ribs for bone to grow, even after coating of the pegs. Also, it can be used for cemented fixation and the arrangement allows for bone cement to attach to and between the ribs, thus providing improved fixation.

In FIG. 9c, the root diameter $D_{60}$ is smaller than the rib diameter $D_{90}$. The stem portion 62 includes three ribs 90 and the head portion 64 includes a rib 90', all of a common diameter. In comparison to the peg of FIG. 9b, this peg has a wider diameter stem 80 and has thinner, shorter ribs 90, 90'.

In FIG. 9d, the root portion 60 has a core with a diameter $D_{80'}$ that is marginally smaller than the diameter $D_{80}$ of the core 80 of the stem portion 62. The ribs 90, 90' all have a common diameter, larger than the root diameter $D_{60}$. In comparison to the peg of FIG. 9c, this peg has thicker ribs 90, 90'. It also only has two ribs 90 on the stem portion 62.

In FIG. 9e, the rib 90' on the head portion 64 has a diameter $D_{90'}$ slightly smaller than the diameter $D_{90}$ of the ribs 90 on the stem portion 62.

Pegs comprising different combinations of the features illustrated and described above may be provided.

The head portion 64 can be wider than the stem portion 62. In certain embodiments, the head portion 64 may be narrower than the root portion 60. At least the stem portion 62 may be tapered, narrowing away from the root portion 60. Tests have shown that the root portion 60 is preferably narrower than the ribs 90, 90'. The head portion 64 can be wider, the same size or narrower than root portion 60, but better purchase is achieved with same width as the ribs 90.

As well as the chamfer to the head portion 64, the ribs 90, 90' are barbed, with a chamfered surface 91 extending at an angle α between the core 80 and the free end of the rib 90 (see FIG. 9b). An objective of the chamfered head 64 and/or the barbed ribs 90 is to maximise the push in/pull out force ratio for the pegs 16 and, therefore, for the component 10. The angle α may be <45 degrees, more specifically <30 degrees.

As shown in FIG. 3, the pegs 16 extend parallel to one another. Alternatively, in certain embodiments the pegs may diverge from one another.

The set of pegs may also comprise greater or fewer than six pegs 16. It will be appreciated that the pegs 16 do not have to be evenly spaced from one another or from the edge 18.

It is preferred for all of the pegs 16 on the component to be of a common form—i.e. to have the same overall shape and dimensions as one another. This may be advantageous for ease of manufacture and for mitigating against bone loss.

However, in certain embodiments it is envisaged that they may have different lengths or diameters, as may be appropriate for securement in different parts of the peripheral portion 104b of the glenoid cavity 104, for example to accommodate different viable bone depths or other properties of the glenoid 102.

Rather than pegs 16 as described above, other sorts of pegs and fixation elements are also envisaged, such as curved protrusions to promote stability, conic shapes for tapering with bone, cubic protrusions, and sharp edges to perforate an upper layer of the bone surface.

The component 10 is manufactured from one or more materials selected from, by way of example: stainless steel, cobalt chromium, titanium, and suitable alloys thereof; ceramic; Silicon nitride; pyrocarbon; carbon-reinforced PEEK; PEEK, PE (VitaE PE, Xlink PE, Normal PE), and PCU. It may be coated, at least partially—for example on the glenoid-contacting surface 14 and/or on the pegs 16—with a material that encourages osseointegration.

The shape of the component 10 may be determined pre-operatively, through known techniques including the use of computer-assisted image methods based on three-dimensional images of the patient's anatomy reconstructed from MRI, CT, ultrasound, X-ray, or other three- or two-dimensional medical scans of the patient's anatomy.

In the pre-operative planning stage, imaging data of the relevant anatomy of a patient can be obtained using one of medical imaging methods described above, as needed for joint modeling, mechanical/alignment axis determination or for other alignment purposes. The imaging data obtained and other associated information can be used to construct a three-dimensional computer image of the relevant portion of the anatomy of the patient. An initial pre-operative plan can be prepared for the patient in image space and can include bone or joint preparation, planning for resections, milling, reaming, broaching, implant selection and fitting, as well as designing patient-specific guides, templates, tools and alignment methods for the surgical procedure.

Figure 6:
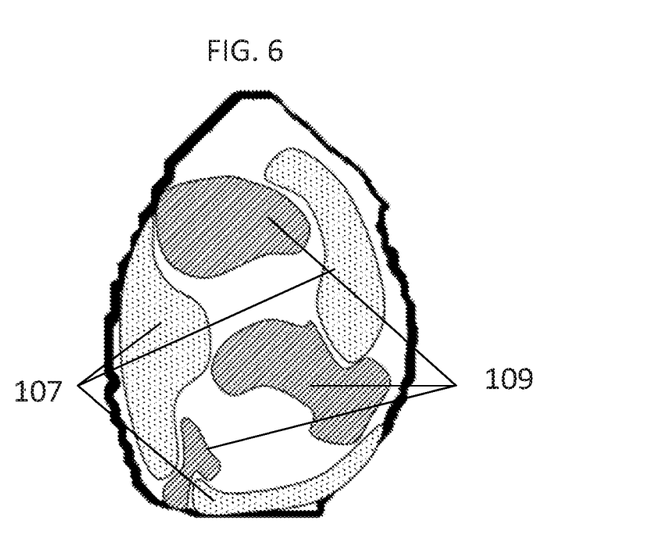
FIG. 6 shows a glenoid cavity on which are mapped different areas representing different bone strengths.
Figure 7:
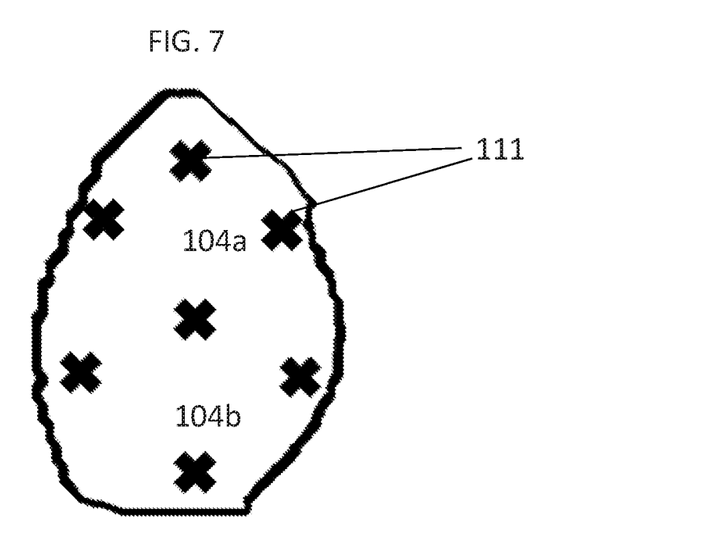
FIG. 7 shows a corresponding map of peg locations determined according to the mapping of FIG. 6.

Specifically, the imaging data can be used to determine the a patient-specific shape for the component 10, including contours of the external bearing surface 12 and the glenoid-contacting surface 14 and the depth and configuration of the sidewall 18, as well as the location of the fixation features 16. In particular, and with reference to FIGS. 6 and 7, the imaging data can be used to determine parameters such as: bone strength (contours 107, 109 of differing strengths shown in FIG. 6); bone stiffness; bone density; and glenoid vault depth. The penetrating force can be estimated by reference to relevant medical literature. FIG. 6 is a map that shows the areas 107, 109 with stronger subchondral bone for the pegs to be anchored in. This was obtained by compiling data from CT scans, material distributions and literature of tests on different areas of the glenoid articulating surface. One or more of those parameters may be taken into account when determining where to position the pegs 16, with a view to placing the pegs (or other fixation elements) at optimum anchor locations 111 within the peripheral portion 104b. By way of example, the anchor points 111 may be selected to be within areas of the peripheral portion 104b corresponding with the highest bone strength areas 107 whilst also ensuring adequate spacing between the anchor points 111 and allowing for manufacturability of the pegs 16.

The outline shape of the component 10 may also be selected based on the imaging data, for example to match the anatomic tear-drop or pear-shaped profile of the glenoid 102.

In this way, the glenoid component 10 can be made to be fully patient-specific. Such a component 10 may conveniently be manufactured using additive manufacturing techniques.

Rather than being made to be fully patient-specific, a more generic-shaped component blank can be provided, with only certain features tailored to suit a particular patient's requirements. For example, a generic blank can be provided, with only the pegs 16 being located according to the patient's particular glenoid structure, as described above. This may be advantageous to reduce the pre-operative planning phase and to streamline the design and manufacture steps. Patient-specific bearing and/or glenoid-contacting surfaces 12, 14 can be incorporated too, within the generic outline profile of the blank.

A range of different sizes of blanks can be provided to accommodate different-sized patients; for example, small, medium and large components. Likewise, a range of differently shaped blanks can also be provided; for example in tear-drop, pear-shaped and oval configurations. With a greater number of options, a greater sized inventory of blanks must be maintained, so it is preferable to keep the number of options to a minimum reasonable whilst still providing adequate fit to the patient. The asymmetrical anatomical tear-drop shaped blanks are side-specific, so requiring an inventory covering both left- and right-side fittings. That is not the case for symmetrical shapes (e.g. the pear-shaped or oval shapes), which therefore require only half the inventory as for asymmetrical shapes.

Furthermore, instead of determining the location of the pegs 16 by reference to pre-operative patient-specific data, the pegs 16 can be located at generic positions in the peripheral portion 17 of a generic component 10. Typically, the generic locations would be determined to provide optimum positioning for the fixation elements 16 across as broad a range of patients as possible. This would eliminate the need to design and manufacture patient-specific components; a ready stock of generic components 10 could be kept available for use.

To fit the component 10 in position on the patient's glenoid 102, a surgeon would prepare the surface of the patient's glenoid 102, resecting a portion of the glenoid cavity 104 so as to be sized and shaped to match the contours of the glenoid-contacting surface 14 of the pre-operatively determined component 10 and, preferably, the outline profile defined by the side wall 18. The resected volume would thus be sized and shaped such that the component 10 will, once fitted in place, be in the correct position with respect to the patient's humeral head (or humeral head prosthesis, if that is also being replaced), the external bearing surface 12 thus being in registration with the humeral head for articulation therewith and the component being substantially contiguous with the topology of the surrounding bone. The surgeon would then prepare the resected surface by drilling or otherwise forming holes at the pre-operatively determined anchor locations 111. These bone preparation steps are preferably carried out through one or more minimally-invasive incisions.

Figure 12:
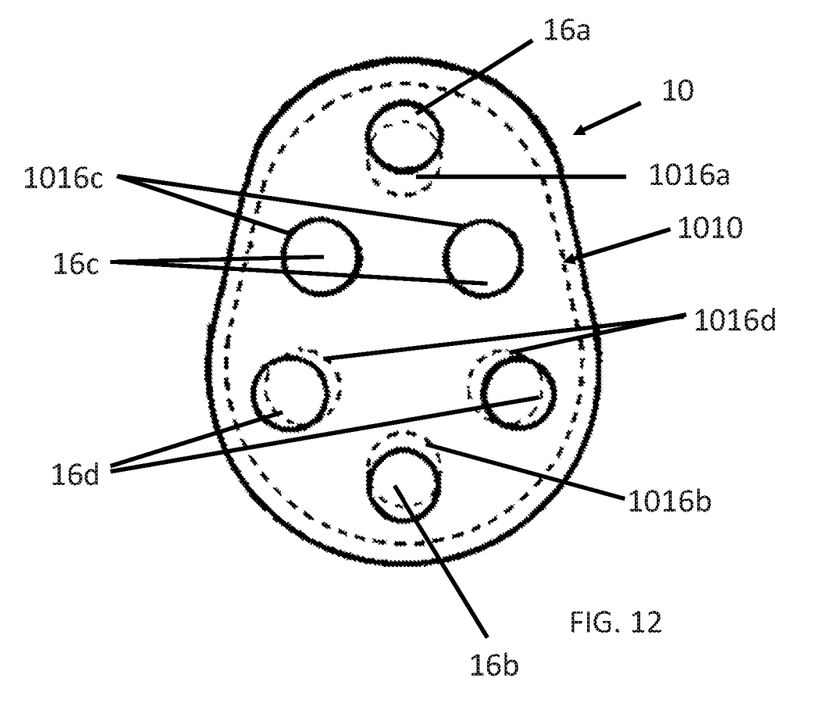
FIG. 12 schematically depicts peg locations for a guide (or a prosthetic component) and, superimposed in dashed lines, for a relatively smaller guide or prosthetic component), showing that there are two common peg locations across the different sized guides (components) to provide alignment and intra-operative revision options.

The component 10 can then be inserted, typically through one of the minimally-invasive incisions, to be fitted in place. The pegs 16 are received in the holes with an interference fit for cementless attachment of the component 10 to the bone, with the glenoid-contacting surface 14 being brought into contact with the resected bone surface.

Where an inventory of components 10 is provided for attachment to differently shaped resected glenoid cavities 104, at least one of the pegs 16 in each component across the inventory is preferably positioned in a common reference location on the component. The principle is illustrated in FIG. 12 which shows the glenoid-contacting side of a first component 10 corresponding to that shown in FIG. 4. Superimposed thereon is a second, smaller component 1010. The pegs 1016 of the second component 1010 are generally closer together, due to the smaller size of the component and the fact that it would be inserted in a correspondingly smaller glenoid cavity 104. However, each of the pair of superior middle pegs 1061c is located in exactly the same position as their counterparts 16c of the first component 10, a specific fixed distance apart. Rather than the two superior middle pegs 16c, 1016c being at the common reference location on the component, it could instead be the inferior pegs 16, 1016d or the pegs 16a, 16b on the superior-inferior axis that define said common reference location across the entire inventory. Indeed, any combination of pegs could be used.

The provision of a common reference location facilitates intra-operative adaptation of the surgical procedure, for example where it becomes evident to the surgeon that a differently-sized or shaped component 10 to that specified in the pre-operative plan is needed. The surgeon would first test a component in situ by trialling the position using only the peg(s) at the common reference location for a temporary trial fit. To this end, the surgeon would first prepare only the hole(s) associated with the common reference location. If the component is considered to be the correct one, then it can be removed from the temporary position and the remaining holes prepared to receive the other pegs and the attachment of the first component can be completed.

If, on the other hand, the first component is deemed unsuitable, then it can be replaced with a second, different one. Since the second component would also have pegs at the common reference location, it would not be necessary to alter the holes made for testing the first component and the second component can be tested in situ just as the first was. If satisfied that the second component is suitable, then the holes for the remaining pegs of that second component can be prepared and the attachment of the second component can be completed. This approach avoids the unnecessary preparation of holes that may not be required (e.g. the holes associated with the pegs of the first component not at the common reference location) and which might otherwise cause difficulties in securing the second (or subsequent) components—for example because the holes for the first component would overlap with the locations for the corresponding holes on the second component, resulting in oversized or wrongly-shaped holes.

The provision of a common reference location also improves alignment of the implant.

Figure 11:
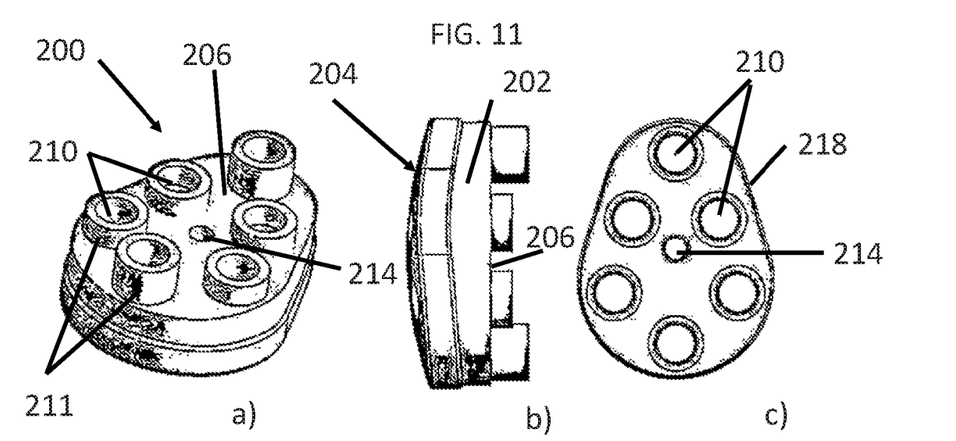

To assist in the preparation of the patient's glenoid cavity to receive a prosthetic glenoid component 10, a guide 200 may be provided, as shown in FIG. 11.

The guide comprises a body 202 with a glenoid-contacting surface 204 on one face thereof, matching that 14 of an associated prosthetic glenoid component 10. An opposite face 206 is spaced from the glenoid-contacting surface 204 by a side wall 208 which defines a thickness of the guide body 202. The side wall 208 preferably matches that 18 of the associated component 10, and would be received, in use, in the resected bone cavity so that the guide is positioned in a unique orientation, corresponding to the eventual in situ position of the associated component.

A plurality of guide apertures 210 extend through the body 202, with each aperture 210 being positioned in registration with the respective location of the associated peg 16 of the associated component 10. As illustrated, each aperture 210 is further defined by a respective annular projection 211 on the face 206, such that the guide apertures 210 have a depth in the range of 5 mm to 20 mm. Instead of the additional depth being provided by the annular projections 211, the body 202 itself may instead be thicker.

By virtue of the guide 200 being positioned in the unique orientation, a drill bit can be guided, in use, through the guide apertures 210 to result in the formation of the requisite fixation holes at the correct predetermined anchor positions 111 for the particular component 10. The depth of the guide apertures 210 ensures that the drill bit is inserted axially therethrough; off-axis movements being prevented by the internal walls of the apertures, so that the resulting fixation holes are accurately located on the patient's glenoid cavity 104.

As an alternative to the glenoid-contacting surface 204 of the guide matching the glenoid-contacting surface 14 of the component 10, and therefore also matching the resected bone surface, the surface 204 may instead be contoured, with the contours matching those of the patient's glenoid prior to any bone preparation steps. Thus, the contoured surfaces may interact to ensure that the guide is positioned in a unique orientation, corresponding to the eventual in situ position of the associated component. This embodiment provides for the preparation of the holes to receive the pegs before any resection of the patient's glenoid cavity 104. The side wall 208 of the guide may also be used to guide in preparation of the glenoid cavity 104 to receive the component (i.e. to guide at least a preliminary part of the resection reaming procedure.

As known in the art, certain procedures require the insertion of a guide wire, and an associated drilling step. In certain embodiments, therefore, the guide 200 may include a further, central guide aperture 214 for guiding a drill bit in the preparation of the guide wire hole.

Figure 8:
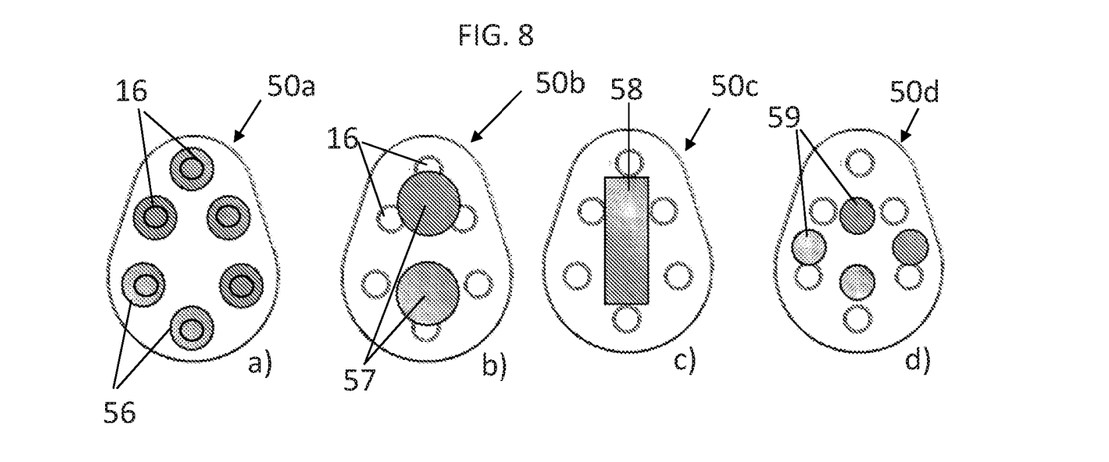
FIGS. 8a to 8d depict how a primary prosthetic glenoid component according to one embodiment of the invention can be replaced in a revision procedure, with a revision glenoid component using: cemented peripheral fixation elements (FIG. 8a); cemented or cementless central pegged fixation (FIG. 8b); cemented central keel fixation (FIG. 8c); or reverse baseplate glenoid screwed attachment (FIG. 8d)

As well as the above-described advantages resulting from the location of the pegs 16 only within the peripheral region 17 of the glenoid-contacting surface 14 of the component 10, an additional benefit is that this configuration leaves the central region 104a of the glenoid cavity undamaged, and there is no violation of the glenoid vault, meaning that it remains available for use in a revision procedure, for example using a standard cemented implant—this allows the implant according to the invention to be used in younger patients or patients with high expected longevity. The short pegs and the peripheral location of them means that the deeper bone is still available for conventional fixation. FIG. 8 shows some different options for revision procedures.

In FIG. 8a, the existing peripheral holes in the glenoid cavity 104 that had received the pegs 16 may be enlarged so as to receive a revision glenoid component 50a having a set of peripheral pegs 56, shown hatched, in substantially the same locations as the pegs 16 of the primary component 10, but for cemented fixation within the enlarged holes.

In FIG. 8b, the revision component 50b comprises a pair of pegs 57, shown hatched, centrally, in-board of the locations of the pegs 16 of the primary component 10, for receipt in corresponding holes in the central region 104a of the glenoid cavity 104. Similarly, in FIG. 8c, the revision component 50c comprises a keel 58, shown hatched, centrally, in-board of the locations of the pegs 16 of the primary component 10, for receipt in a corresponding hole in the central region 104a of the glenoid cavity 104. Each of the revision components 50b and 50c would typically be secured to the underlying glenoid cavity 104 by a cemented fixation.

An alternative revision component 50d is shown in FIG. 8d. Here, a reverse glenoid baseplate is screwed into position; the glenoid baseplate of a reverse implant usually has a few metal pegs that are press fit into the bone and then two to four screws are used to secure it in place. These are screwed through the baseplate through specifically created holes.

In certain embodiments, particularly where a guide wire is used to reference the fixation positions and where a central hole has therefore been made to receive the guide wire, an additional central peg (not shown) may also be provided in the central portion 15 of the glenoid-contacting surface 14 of the component 10. In such embodiments, each of the pegs— the peripheral pegs 16 and the central peg—are all of an equal size. Here, equal size means at least of equal diameter, although it is envisaged that the pegs may have different lengths. Alternatively, each of the pegs has the same diameter to length ratio.

In any event, the pegs are much smaller than those of the prior art. Secure fixation is assured by virtue of the provision of the plurality of pegs 16 in the peripheral portion 104b of the glenoid cavity and their anchoring in the stronger shallow layer of subchondral bone, as well as the particular form of the pegs 16 to resist pull-out forces and a rocking-horse effect. The central peg, if present, can therefore be made small, sized only to fit within the pre-existing guide wire hole and thereby providing some additional pull-out resistance and shear resistance and yet not significantly compromising on the structural integrity of the central portion 104a of the glenoid cavity, in contrast to the relatively large pegs or stems traditionally used to secure prosthetic glenoid components in that central portion.

The term 'minimally-invasive' in the context of a surgical procedure is considered to have an established meaning within the art and is intended to encompass, inter alia, arthroscopic and mini-open surgical approaches, including those using multiple minimally-invasive incisions.

It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail. Accordingly, individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure as defined by the accompanying claims.

The invention claimed is:

1. A prosthetic glenoid component comprising:
a concave external bearing surface;
a glenoid-contacting surface opposite to the bearing surface; and
a plurality of fixation elements protruding from said glenoid-contacting surface oppositely to said bearing surface for location into a peripheral portion of a glenoid cavity to secure the component to the scapula, wherein a central portion of the glenoid-contacting surface is free of fixation elements,
wherein the fixation elements are arranged substantially equidistantly from an outer edge of the component,
wherein one of the fixation elements is located at a superior end of the component, one of the fixation elements is located at an inferior end of the component, and at least two of the fixation elements are located either side of a superior-inferior axis of the component, and
wherein at least two further fixation elements of the plurality of fixation elements are located either side of the superior-inferior axis at a position more inferior or more superior than the at least two of the fixation elements.

2. The component of claim 1, wherein all fixation elements protruding from said glenoid-contacting surface are of a common size.

3. The component of claim 1, wherein the component has a superior end with a first radius of curvature and an inferior end with a second radius of curvature, larger than the first radius of curvature, and
wherein: at least one of the respective centres of the first and second radii of curvature is co-linear along a superior-inferior axis of the component; one of the respective centres of the first and second radii of curvature is off-set from a superior-inferior axis of the component; or both.

4. The component of claim 1, wherein the component is symmetrical about a superior-inferior axis.

5. The component of claim 1, wherein at least the glenoid-contacting surface is sized and shaped to substantially match the geometry of a patient's resected glenoid cavity.

6. A prosthetic glenoid component comprising:
a concave external bearing surface;
a glenoid-contacting surface opposite to the bearing surface; and
a plurality of fixation elements protruding from said glenoid-contacting surface oppositely to said bearing surface for location into a peripheral portion of a glenoid cavity to secure the component to the scapula, wherein a central portion of the glenoid-contacting surface is free of fixation elements,
wherein the fixation elements are arranged substantially equidistantly from an outer edge of the component,
wherein one of the fixation elements is located at a superior end of the component, one of the fixation elements is located at an inferior end of the component, and at least two of the fixation elements are located either side of a superior-inferior axis of the component, and
wherein the fixation elements comprise pegs, each peg comprising a root portion adjacent to said glenoid-contacting surface and a stem portion and a central axial core, such that the root portion is wider than the central axial core and an interface between the root portion and the glenoid-contacting surface is fileted.

7. The component of claim 6, each peg further comprises a head portion at a free end thereof such that the root, stem, and head portions are contiguous with one another, and
wherein the head portion is chamfered such that it is wider than the central axis core and narrower than the root portion.

8. The component of claim 6, wherein each peg further comprises a plurality of circumferential ribs, wherein the plurality of circumferential ribs are disposed along the length of the core, disposed over at least the stem portion, or both.

9. The component of claim 8, wherein the diameter of at least one of the ribs on the stem portion is greater than the diameter of the root portion.

10. The component of claim 8, wherein each peg further comprises a head portion at a free end thereof, and wherein at least one of the ribs is disposed on the head portion.

11. The component of claim 8, wherein the ribs all have the same diameter, and wherein each rib has a width to length ratio of less than 1:1.

12. The component of claim 8, wherein at least one of the ribs is barbed.

13. The component of claim 6, wherein each peg has a diameter to length ratio in the range of 2:1 to 1:2.

14. The component of claim 6, comprising six pegs, the six pegs extending parallel to one another or diverging from one another.

15. The component of claim 1, manufactured from a material selected from: stainless steel, cobalt chromium, titanium, and suitable alloys thereof; ceramic; Silicon nitride; pyrocarbon; carbon-reinforced PEEK; PEEK, PE (VitaE PE, Xlink PE, Normal PE), and PCU, and wherein the component is further configured to comprise an osseoconductive coating on at least one of the glenoid-contacting surface and the plurality of fixation elements.

16. An inventory of prosthetic glenoid components for attachment to differently shaped resected glenoid cavities, each component being a prosthetic glenoid component comprising:
a concave external bearing surface;
a glenoid-contacting surface opposite to the bearing surface; and a plurality of fixation elements protruding from said glenoid-contacting surface oppositely to said bearing surface for location into a peripheral portion of a glenoid cavity to secure the component to the scapula, wherein a central portion of the glenoid-contacting surface is free of fixation elements, wherein the fixation elements are arranged substantially equidistantly from an outer edge of the component, wherein one of the fixation elements is located at a superior end of the component, one of the fixation elements is located at an inferior end of the component, and at least two of the fixation elements are located either side of a superior-inferior axis of the component, and wherein: at least one of the fixation elements in each component across the inventory is positioned in a common reference location; at least two of the fixation elements in each component across the inventory are positioned in common reference locations a specific fixed distance apart; or both.

17. A guide for preparing a patient's glenoid cavity to receive the prosthetic glenoid component according to claim 1, the guide comprising:
a body with a glenoid-contacting surface matching that of the prosthetic glenoid component; and
a plurality of guide apertures having a depth in the range of 5 mm to 20 mm, extending through the body and positioned in registration with the respective locations of the plurality of fixation elements on the prosthetic glenoid component, for guiding a drill bit, in use, to drill fixation holes in the patient's glenoid cavity to accommodate said plurality of fixation elements.

18. A kit comprising:
the prosthetic glenoid component according to claim 1; and
an associated guide for preparing a patient's glenoid cavity to receive the prosthetic glenoid component, the guide comprising:
a body with a glenoid-contacting surface matching that of the prosthetic glenoid component; and
a plurality of guide apertures having a depth in the range of 5 mm to 20 mm, configured to extend through the body and be positioned in registration with the respective locations of the plurality of fixation elements on the prosthetic glenoid component, for guiding a drill bit, in use, to drill fixation holes in the patient's glenoid cavity to accommodate said plurality of fixation elements,
wherein the kit further comprises an associated drill bit sized for receipt through the guide apertures for drilling said fixation holes.

19. The prosthetic glenoid component of claim 1, wherein the plurality of fixation elements comprises six fixation elements.

* * * * *